United States Patent

Motisi et al.

[11] Patent Number: 5,843,046
[45] Date of Patent: Dec. 1, 1998

[54] CATHETER APPARATUS

[75] Inventors: Paul J. Motisi, 6129 N. Navarre, Chicago, Ill. 60631; Dale Tokarz, Chicago, Ill.; Bruce Flesher, Hampshire, Ill.

[73] Assignee: Paul J. Motisi, Chicago, Ill.

[21] Appl. No.: 864,935

[22] Filed: May 29, 1997

[51] Int. Cl.⁶ .................................................. A61M 5/00
[52] U.S. Cl. ...................... 604/256; 604/247; 604/164
[58] Field of Search ..................... 604/164, 167, 604/169, 246, 256, 247

[56] References Cited

U.S. PATENT DOCUMENTS

| | | | |
|---|---|---|---|
| 3,848,579 | 11/1974 | Villa-Real . | |
| 4,392,499 | 7/1983 | Towse . | |
| 4,610,665 | 9/1986 | Matsumoto et al. | 604/167 |
| 4,929,235 | 5/1990 | Merry et al. . | |
| 4,960,412 | 10/1990 | Fink | 604/167 |
| 4,967,762 | 11/1990 | DeVries . | |
| 4,972,843 | 11/1990 | Brodén . | |
| 5,080,654 | 1/1992 | Picha et al. | 604/167 |
| 5,106,054 | 4/1992 | Molenauer et al. | 251/149.1 |
| 5,125,903 | 6/1992 | McLauglin et al. | 604/167 |
| 5,199,948 | 4/1993 | McPhee | 604/86 |
| 5,313,969 | 5/1994 | Hsieh . | |
| 5,685,866 | 11/1997 | Lopez | 604/249 |

FOREIGN PATENT DOCUMENTS 0055657  7/1982  European Pat. Off. .

Primary Examiner—John D. Yasko
Assistant Examiner—Deborah Blyveis
Attorney, Agent, or Firm—Speckman Pauley Petersen & Fejer

[57] ABSTRACT

A catheter apparatus having a housing with a throughbore. A seal is mounted within the throughbore. The seal has a peripheral sealing surface that contacts an external surface of a sleeve when the sleeve is mounted within the throughbore. A one-way valve or check valve is mounted within the throughbore, preferably between the peripheral sealing surface and the sleeve. When the sleeve is withdrawn from the throughbore, the one-way valve prevents fluid, such as a blood sample, from flowing outside of the housing.

14 Claims, 5 Drawing Sheets

CATHETER APPARATUS

BACKGROUND OF THE INVENTION

FIELD OF THE INVENTION

This invention relates to a catheter apparatus that is preferably used to draw a blood sample from a patient, discharge the blood sample onto a test surface and then connect an intravenous tube to the catheter apparatus, while preventing blood from flowing through the catheter apparatus while removing the blood sample and attaching an intravenous connection.

DESCRIPTION OF PRIOR ART

U.S. Pat. No. 4,929,235 discloses a self-sealing catheter introducer which forms a seal and prevents blood or other fluid leakage. Two different gaskets are positioned within a flow chamber of a body. A first gasket has a Y-slit and a flange and the second gasket which is spaced from the first gasket, has a hole that terminates in a conical portion which points toward the first gasket. The Y-slit gasket is rigid enough to maintain a seal against a blood pressure when a catheter is withdrawn from the body.

European Patent Specification 0 055 657 discloses an instrument for taking a blood sample. A syringe is connected to a tubular receptacle that has an end cap which accommodates a first needle. A second needle, at an opposite end of the syringe, passes through a rubber sealing disc mounted within the tubular receptacle. With the first needle inserted into a vein, a syringe piston is used to draw blood into the receptacle. When the second needle is removed from the sealing disc, the elasticity of the sealing disc material closes a hole formed within the sealing disc.

U.S. Pat. No. 3,848,579 discloses a blood-drawing device that has an elasto-valvular component with equally dimensioned valvular slits. The elasto-valvular component is mounted within a bulbous body.

U.S. Pat. No. 4,972,843 discloses a blood-sampling apparatus having a front needle and a rear needle with ends that face away from one another. The front needle pierces a vein or a blood vessel. The pointed end of the rear needle pierces a sealing stopper of a vacuum-type test tube. A mechanical flow regulator is positioned between both needles and regulates flow through the needles.

U.S. Pat. No. 4,392,499 discloses a tubular adaptor for blood-sampling purposes. The tubular adaptor is positioned between a catheter and a needle. A tapered socket fitting enables either blood sampling or intravenous feeding through the same catheterized situs.

U.S. Pat. No. 5,313,969 discloses a blood-sampling tube that reduces pressure as the blood flows in a downstream direction. Various flow paths through the device reduce pressure of the blood prior to dumping the blood in a reservoir. The needle extends through an elastic cork.

U.S. Pat. No. 4,967,762 discloses a biopsy syringe that has a needle hub. Once the needle is inserted into a specimen, a vacuum is pulled on a needle lumen and tissue is drawn into the lumen. A suction vent releases the vacuum on the needle lumen and allows the needle to be withdrawn without diluting the specimen.

It is apparent from the teachings of the prior art that a need exists for a catheter apparatus that can be used to draw a blood sample from a patient, remove the blood sample from the catheter apparatus, discharge the blood sample onto a test surface and then attach an intravenous connection to the catheter apparatus, all while containing the patient's blood within the catheter apparatus. There is also a need for a catheter apparatus that requires only one hand to operate the insertion, blood-sampling, blood-testing and intravenous connection tasks, so that the user may have a free hand to control a patient.

SUMMARY OF THE INVENTION

It is one object of this invention to provide a catheter apparatus that accommodates a conventional intravenous needle.

It is another object of this invention to provide a catheter apparatus that allows a blood sample to be withdrawn from the catheter apparatus while preventing blood from flowing outside of the catheter apparatus.

It is another object of this invention to provide a catheter apparatus that can be used to attach an intravenous connection.

It is still another object of this invention to provide a catheter apparatus that can be introduced into a patient and operated with only one user's hand.

It is yet another object of this invention to provide a catheter apparatus that is constructed of relatively inexpensive elements and with relatively few moving mechanical parts.

The above and other objects of this invention are accomplished with a catheter apparatus having a plunger piston mounted within a chamber of a sleeve. A seal forms a hermetic seal when the sleeve is inserted within a throughbore of a housing or body of the catheter apparatus. A one-way valve is either separately mounted within the throughbore or is integrally formed with the seal. A sheath is mounted with respect to the housing, preferably so that a portion of the sheath is within the throughbore and a remaining portion of the sheath extends from the housing. When attached to a patients body, the sheath is preferably inserted within a vein or a blood vessel of the patient and acts as a conventional catheter.

The plunger piston seals an upper portion of a chamber formed within the sleeve. A needle is attached to one end of the sleeve. When the sleeve is in a mounted position within the throughbore, the needle preferably passes through at least one slit within a bulbous end portion of the seal. The bulbous end portion of the seal preferably expands to accommodate the needle and also to form a seal around the outside surface of the needle.

When the needle and the sheath are inserted into a patient's vein or blood vessel, blood flows through the needle into the chamber of the sleeve. The plunger piston stops the blood from the flowing outside of the chamber of the sleeve. Once a blood sample is received within the chamber, the sleeve and needle can be removed from within the throughbore, leaving the sheath to remain within the patient's vein or blood vessel.

As the plunger piston, sleeve and needle are withdrawn as a unit from the housing, in one preferred embodiment of this invention, the bulbous end portion returns to its initial shape and backpressure from the patient's blood seals the slits within the bulbous end portion of the seal.

Once the plunger piston, sleeve and needle are removed from the housing, the plunger piston can be depressed or slidably forced to move within the chamber and thereby reduce a volume of the chamber to discharge blood from the needle. Depressing the plunger piston allows a user, such as a paramedic or another healthcare worker, to insert the needle and sheath within a patient's vein or blood vessel in a conventional manner, and then remove a blood sample from the catheter apparatus without discharging blood from the catheter apparatus. Because the one-way valve or bulbous end portion of the seal retains the blood, the user no longer needs to use one hand to stop blood flow from the catheter apparatus. After the needle and sheath are introduced into the patient, the user then has both hands free to discharge the blood sample from the chamber, through the needle and onto a test surface, such as a chemical strip.

Once the plunger piston, sheath and needle assembly is removed from the housing, an intravenous tube can be inserted through the seal so that a peripheral sealing surface of the seal contacts an external surface of the intravenous tube.

The catheter apparatus according to this invention requires only one hand to insert the needle and sheath into a patient's vein or blood vessel, to then withdraw the plunger, sleeve and needle assembly which contains the blood sample, to then depress the plunger piston and discharge the blood sample onto a test surface, and to then attach an intravenous connection. With the catheter apparatus according to this invention, the user has a free hand and arm available to hold or otherwise assist the patient, which is particularly important when the patient becomes combative or has seizure activity, for example. If a patient becomes violent or combative and withdraws the intravenous tube from the catheter device, blood will not discharge from the catheter apparatus and thus there is no danger of contamination to healthcare workers or to surrounding equipment.

BRIEF DESCRIPTION OF THE DRAWINGS

The above-mentioned and other features and objects of this invention will be better understood from the following detailed description when taken in view of the drawings wherein.

DESCRIPTION OF PREFERRED EMBODIMENTS

Figure 1:
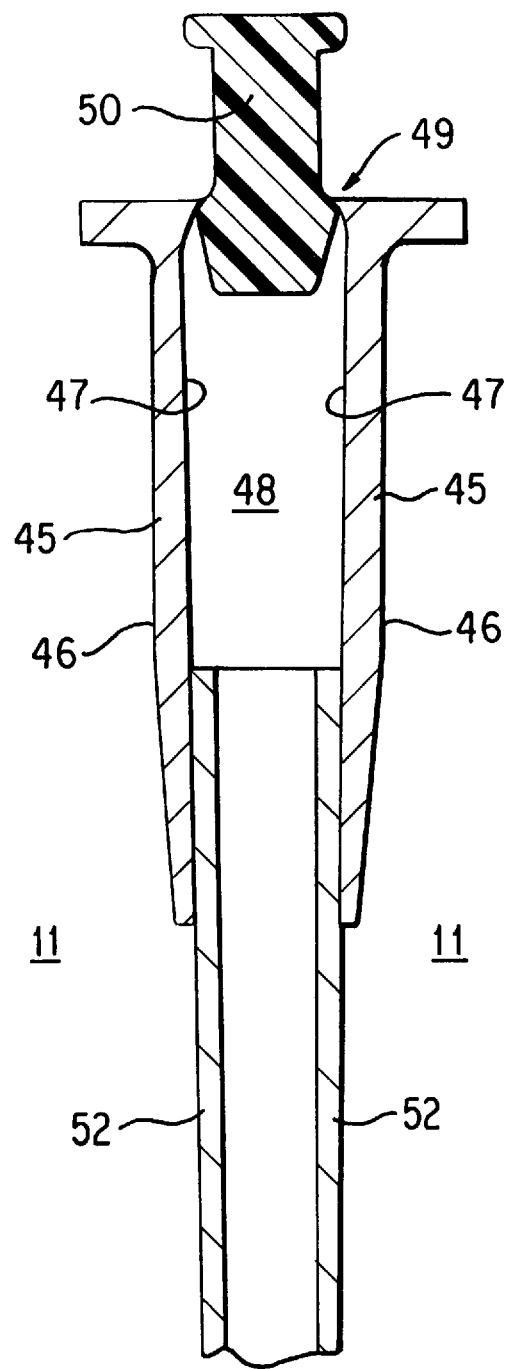
FIG. 1 is a cross-sectional view of a plunger-needle assembly, according to one preferred embodiment of this invention.

FIG. 1 shows a cross-sectional view of a plunger-needle assembly, according to one preferred embodiment of this invention. As shown in FIG. 1, sleeve 45 has a chamber 48 that can be shaped in any suitable manner known to those skilled in the art. As shown in FIG. 1, chamber 48 has a generally circular cross section. Needle 52 is secured with respect to sleeve 45. As shown in FIG. 1, inner surface 47 tapers in an area where needle 52 contacts inner surface 47, thereby forming a press-fit connection between sleeve 45 and needle 52. Needle 52 may comprise any suitable conventional needle known to those skilled in the art. Needle 52 preferably but not necessarily has a constant outside diameter. It is apparent that needle 52 can be attached or connected with respect sleeve 47 in any manner known to those skilled in the art, preferably so that a blood sample or other fluid within chamber 48 is prevented from leaking or passing between sleeve 45 and needle 52 to surrounding ambient 11.

Figure 2:
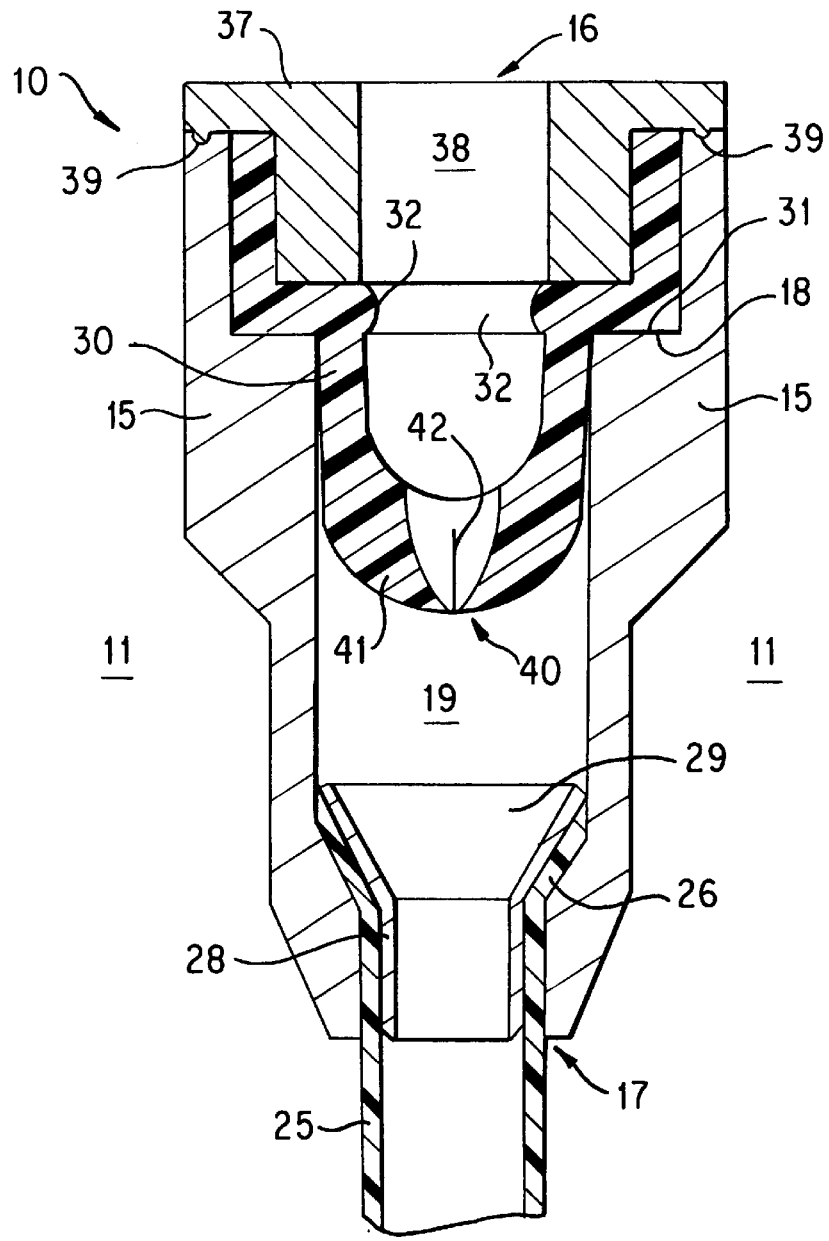
FIG. 2 is a cross-sectional view of a seal and a sheath both mounted within a throughbore of a housing, according to one preferred embodiment of this invention.

Still referring to FIG. 1, plunger 50 closes open end portion 49 of sleeve 45. Open end portion 49 is in communication with chamber 48. As shown in FIG. 1, plunger 50 is slidably mounted within chamber 48. When chamber 48 is filled with a fluid, such as a blood sample, plunger 50 can be depressed or otherwise moved toward needle 52 in order to discharge the fluid through the passageway of the needle 52. As discussed later in this specification, once chamber 48 is filled with a blood sample, the plunger-needle assembly shown in FIG. 1 can be removed from housing 15, as shown in FIG. 2. Plunger 50 can then be moved to discharge the blood sample onto a test surface, such as a chemical strip. It is apparent that, in lieu of plunger 50, other suitable mechanical devices can be used to force the fluid through the passageway within needle 52. For example, a cap found on a conventional eye dropper device or another suitable bulb or other flexible device can be used to discharge the fluid through the passageway of needle 52. However, plunger 50 is particularly advantageous when drawing blood samples because of the ease of operation and cleanliness associated with an embodiment comprising plunger 50.

As shown in FIG. 2, housing 15 has or forms throughbore 19. Housing 15 also comprises inlet 16 and outlet 17, both which are in communication with throughbore 19 in the condition shown in FIG. 2. A portion of sheath 25 is mounted within throughbore 19, according to one preferred embodiment of this invention. It is apparent that sheath 25 can be attached or otherwise secured with respect to housing 15. As shown in FIG. 2, sheath 25 has flared end portion 26 which retains sheath 25 is a mounted position with respect to housing 15. Also as shown in FIG. 2, retainer 28 can be used to retain sheath 25 within throughbore 19. Guide surface 29 of retainer 28 can be used to guide needle 52 into a bore within sheath 25. For example, if needle 52 is positioned askew with respect to a centerline of sheath 25, guide surface 29 can deflect and guide needle 52 in a properly centered direction. Guide surface 29 preferably has a sufficient material hardness that prevents a pointed tip of needle 52 from penetrating guide surface 29. Retainer 28 can thus be used to prolong the useful life of sheath 25. However, it is apparent that sheath 25 can be constructed of a material that resists puncture by the pointed tip of needle 52.

Figure 3:
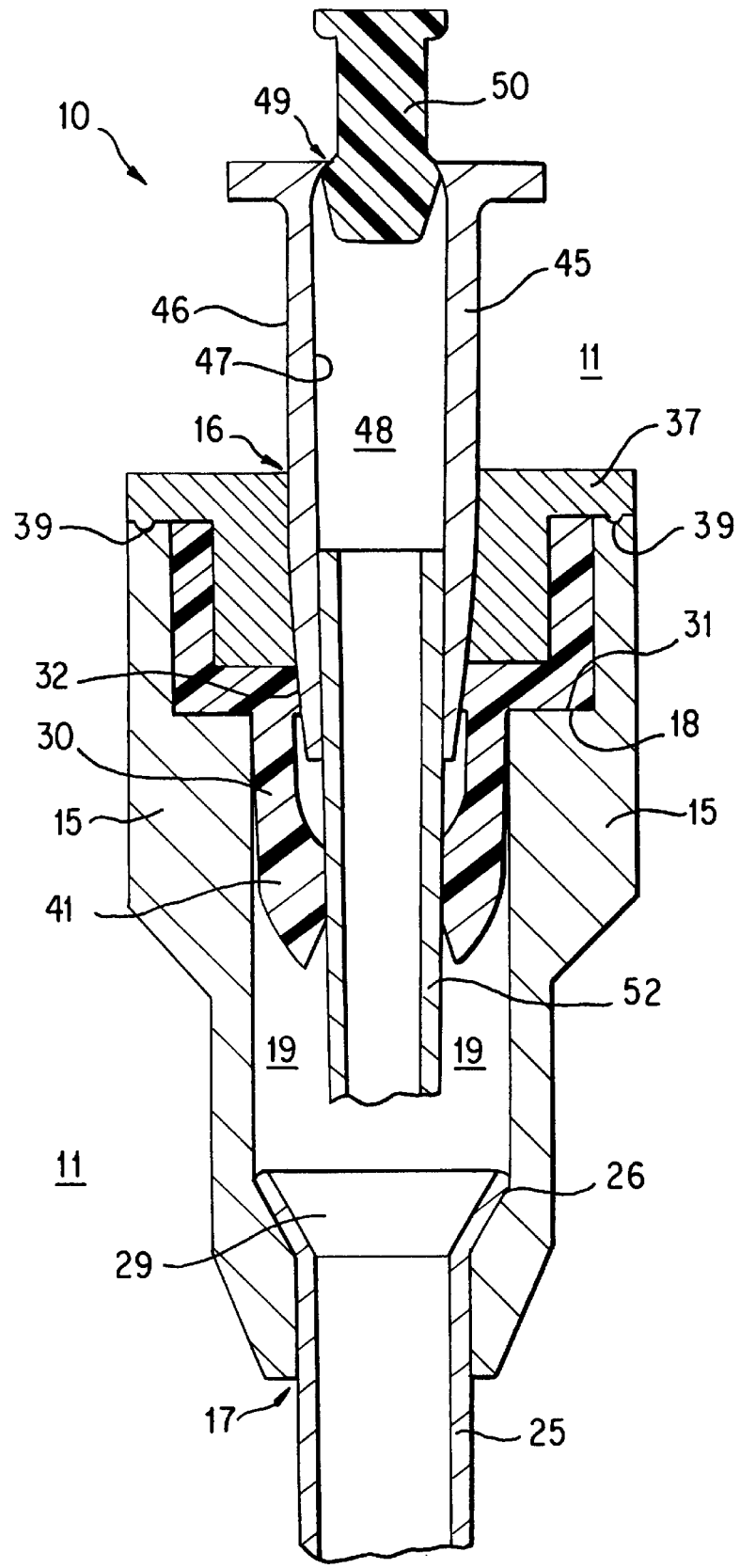
FIG. 3 is a cross-sectional view of a plunger-needle assembly mounted within a throughbore of a housing, according to one preferred embodiment of this invention.

Catheter apparatus 10 of this invention preferably comprises sealing means for forming a seal peripherally about external surface 46 of sleeve 45 when sleeve 45 is positioned within throughbore 19, as shown in FIG. 3, and also for preventing fluid communication within throughbore 19 when sleeve 45 is withdrawn from throughbore 19, as shown in FIG. 2. In one preferred embodiment according to this invention, the sealing means comprise seal 30 mounted within throughbore 19. As shown in FIG. 2, seal 30 comprises shoulder 31 that contacts corresponding shoulder 18 of housing 15. As shown in FIG. 2, seal 30 is preferably maintained in a mounted position with respect to housing 15.

In one preferred embodiment according to this invention, cap 37 is partially mounted within throughbore 19 and retains seal 30 in a mounted position with respect to housing 15. Weld 39, such as an ultrasonic weld, or another suitable means for securing known to those skilled in the art can be used to hermetically seal cap 37 with respect to housing 15. It is apparent that other adhesives, screwed connections or mechanical connections can be used to accomplish the same result of forming a hermetical seal between cap 37 and housing 15, preferably about throughbore 19. Although not necessary, cap 37 and the corresponding hermetic seal with respect to housing 15 can be used to prevent leakage of a blood sample or other fluid within throughbore 19, between seal 30 and housing 15 to surrounding ambient 11.

Cap 37 preferably comprises passageway 38 which is aligned with throughbore 19, as shown in FIG. 2. With sleeve 45 is a mounted positioned within throughbore 19, sleeve 45 is also preferably positioned within passageway 38. In one preferred embodiment of this invention, passageway 38 is approximately cylindrical. In another preferred embodiment of this invention, passageway 38 tapers or diverges in a direction from inlet 16 to outlet 17.

In one preferred embodiment according to this invention, the sealing means further comprise seal 30 having peripheral sealing surface 32 which contacts external surface 46 of sleeve 45 when sleeve 45 is mounted within throughbore 19, as shown in FIG. 3. Sealing surface 32 may have a general O-ring shape as shown in FIG. 2, or may comprise any other suitable surface that forms a seal with respect to external surface 46 and thus prevents a blood sample or other fluid from passing between seal 30 and sleeve 45.

Figure 6:
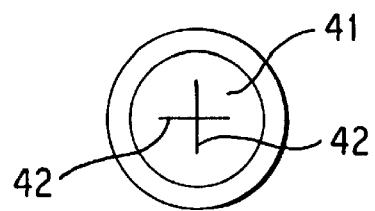
FIG. 6 is an end view of a bulbous end portion having two slits, of a seal, according to one preferred embodiment of this invention.

In another preferred embodiment according to this invention, the sealing means comprise one-way valve 40 mounted within throughbore 19, preferably between peripheral sealing surface 32 and outlet 17. In one preferred embodiment according to this invention, one-way valve 40 comprises seal 30 having bulbous end portion 41. At least one slit 42, preferably two slits 42, are positioned within bulbous end portion 41, preferably but not necessarily in a generally central portion of bulbous end portion 41. FIG. 6 shows one preferred embodiment of bulbous end portion 41, having two slits 42.

Bulbous end portion 41 is preferably constructed of a resilient deformable material, such as a suitable synthetic rubber, plastic or other deformable material known to those skilled in the art. In one preferred embodiment of this invention as shown in FIG. 1 and 2, bulbous end portion 41 is integrated with seal 30. The integrated construction offers may advantages, including reduced costs, structural rigidity and enhanced performance. However, it is apparent that one-way valve 40 and peripheral sealing surface 32 can be constructed as separate elements without departing from the intended result of forming both a sealing surface and a one-way valve or check valve.

As shown in FIGS. 1 and 2, bulbous end portion 41 converges in a direction away from sealing surface 32, or in a direction from inlet 16 toward outlet 17. With such configuration, fluid cannot pass from outlet 17 to inlet 16, which is desirable when sleeve 45 is removed from throughbore 19.

Figure 4:
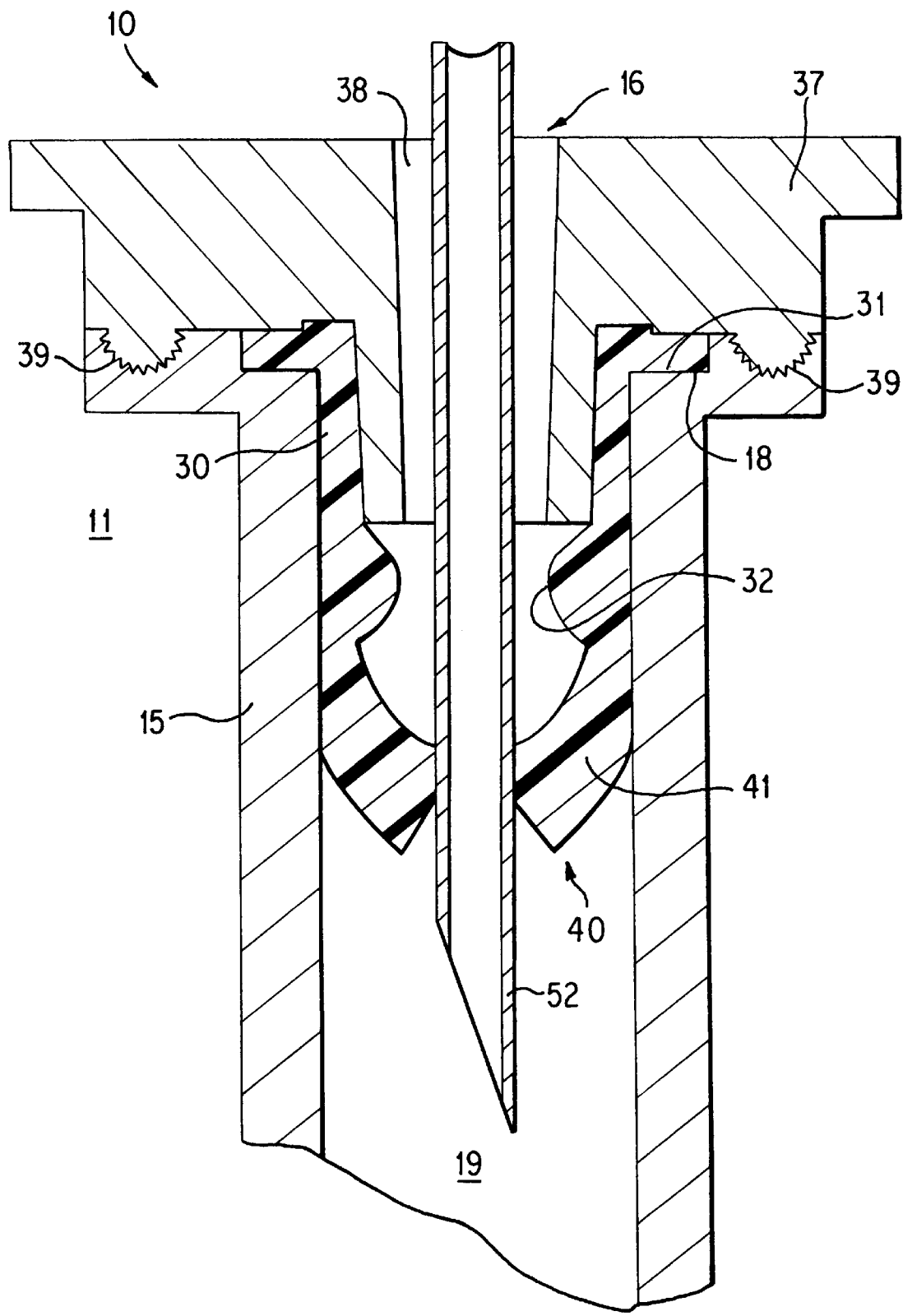
FIG. 4 is a cross-sectional partial view of a needle entering a bulbous end portion of a seal which is mounted within a throughbore of a housing, according to one preferred embodiment of this invention.

FIG. 4 shows needle 52 in a position just after passing through slits 42 of bulbous end portion 41. As shown in FIG. 4, peripheral sealing surface 32 does not contact needle 52 with needle 52 in the position shown in FIG. 4. Once needle 52 punctures a vein or blood vessel, blood flows through needle 52 and into chamber 48, as a result of backpressure from the blood system of the patient. Once chamber 48 is filled, the plunger-needle assembly can be withdrawn from housing 15 and throughbore 19, leaving seal 30 in the condition as shown in FIG. 2. With bulbous end portion 41 closed, as shown in FIG. 2, blood does not flow through slits 42. The blood pressure applies forces to bulbous end portion 41 that maintain slits 42 in a sealed or closed condition.

Figure 5:
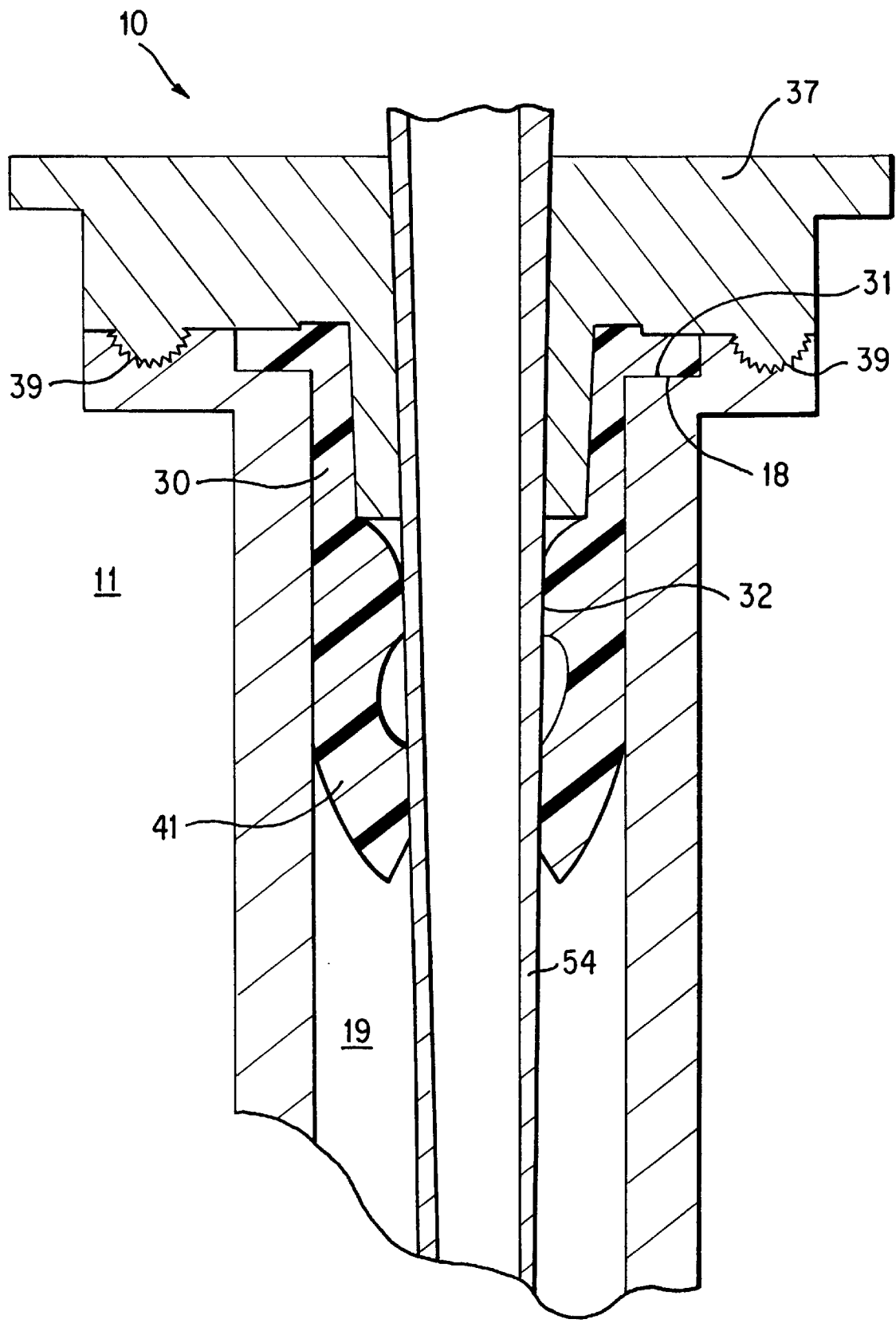
FIG. 5 is a cross-sectional partial view of an intravenous tube mounted within a throughbore of a housing, and passing through a seal, according to one preferred embodiment of this invention.

As shown in FIG. 5, intravenous tube 54 which is preferably tapered can then be inserted within throughbore 19, until sealing surface 32 contacts intravenous tube 54. Depending upon the design of slits 42, bulbous end portion 41 can even be used to provide another seal or a primary seal.

It is apparent that the elements of this invention can be constructed of any suitable material, such as plastic, synthetic rubber, metal or any other suitable composite material, depending upon the particular and intended use. It is also apparent that the shapes of the elements described in the specification and in the claims can be varied without departing from the desired results of this invention.

While in the foregoing specification this invention has been described in relation to certain preferred embodiments thereof, and many details have been set forth for purpose of illustration it will be apparent to those skilled in the art that the invention is susceptible to additional embodiments and that certain of the details described in the specification and in the claims can be varied considerably without departing from the basic principles of the invention.

We claim:

1. A catheter apparatus comprising:
    a housing having a throughbore, a sheath, a portion of said sheath mounted within said throughbore;
    a seal mounted within said throughbore, said seal having a peripheral sealing surface, a one-way valve mounted within said throughbore; and
    a sleeve mounted within said throughbore, said sleeve extending through said peripheral sealing surface with an external surface of said sleeve contacting said peripheral sealing surface, said sleeve having a chamber and an open end portion in communication with said chamber, and a plunger closing said open end portion of said sleeve and slidably mounted within said chamber.

2. A catheter according to claim 1 further comprising a cap, said cap retaining said seal in a mounted position with respect to said housing.

3. A catheter according to claim 2 wherein said cap retains said seal in a mounted position within said throughbore.

4. A catheter according to claim 2 wherein said cap is hermetically sealed about said throughbore and with respect to said housing.

5. A catheter according to claim 2 wherein said cap has a passageway aligned with said throughbore, and said sleeve is positioned within said passageway.

6. A catheter according to claim 1 wherein a portion of said throughbore has a circular cross section.

7. A catheter according to claim 1 wherein said sheath is sealably mounted with respect to said housing forming a hermetic seal between said throughbore and an atmosphere external to said housing.

8. A catheter according to claim 1 wherein said seal has an O-ring section forming said peripheral sealing surface.

9. A catheter according to claim 1 wherein said one-way valve comprises a bulbous end portion having at least one slit positioned in a generally central portion of said bulbous end portion.

10. A catheter according to claim 9 wherein said bulbous end portion is of a resilient deformable material.

11. A catheter according to claim 9 wherein said bulbous end portion is integrated with said seal.

12. A catheter according to claim 9 wherein said bulbous end portion has two said slits and said slits intersect each other.

13. A catheter according to claim 9 wherein said bulbous end portion converges in a direction away from said peripheral sealing surface.

14. A catheter according to claim 1 further comprising a retainer positioned within said throughbore and abutting said sheath, and said retainer having a guide surface for guiding a needle through said sheath.

* * * * *